United States Patent
Wu et al.

(10) Patent No.: US 8,483,471 B2
(45) Date of Patent: Jul. 9, 2013

(54) METHOD AND SYSTEM FOR SCATTER CORRECTION IN X-RAY IMAGING

(75) Inventors: Xiaoye Wu, Rexford, NY (US); Jiang Hsieh, Brookfield, WI (US); Paavana Sainath, Oconomowoc, WI (US); Xin Liu, Waukesha, WI (US)

(73) Assignee: General Electric Company, Niskayuna, NY (US)

(*) Notice: Subject to any disclaimer, the term of this patent is extended or adjusted under 35 U.S.C. 154(b) by 188 days.

(21) Appl. No.: 13/174,480

(22) Filed: Jun. 30, 2011

(65) Prior Publication Data

US 2013/0004050 A1 Jan. 3, 2013

(51) Int. Cl.
*G06K 9/00* (2006.01)
(52) U.S. Cl.
USPC .......................... 382/132; 378/70
(58) Field of Classification Search
None
See application file for complete search history.

(56) References Cited

U.S. PATENT DOCUMENTS

| | | | |
|---|---|---|---|
| 6,876,718 B2 | 4/2005 | Tang | |
| 7,308,072 B2 | 12/2007 | Ruhrnschopf | |
| 7,379,575 B2 * | 5/2008 | Ruhrnschopf | 382/128 |
| 7,583,780 B2 * | 9/2009 | Hsieh et al. | 378/4 |
| 2010/0204563 A1 * | 8/2010 | Stodilka et al. | 600/411 |

OTHER PUBLICATIONS

Thierry, R., et al.; "Hybrid simulation of scatter intensity in industrial cone-beam computed tomography," Nuclear Instruments and Methods in Physics Research A, vol. 598, Issue 2, pp. 611-619.

Brunner, Stephen, et al.; "Prior image constrained scatter correction in cone-beam computed tomography image-guided radiation therapy," Medical Physics, vol. 36, Issue 6, pp. 2258-2268.

Zhu, Lei, et al.; "Scatter correction for cone-beam CT in radiation therapy," Physics in Medicine and Biology, vol. 56, Issue 4, pp. 1015-1030.

* cited by examiner

*Primary Examiner* — Claire X Wang
(74) *Attorney, Agent, or Firm* — Marie-Claire B. Maple

(57) ABSTRACT

Approaches for deriving scatter information using inverse tracking of scattered X-rays is disclosed. In certain embodiments scattered rays are tracked from respective locations on a detector to a source of the X-ray radiation, as opposed to tracking schemes that proceed from the source to the detector. In one such approach, the inverse tracking is implemented using a density integrated volume that reduces the integration steps performed.

20 Claims, 5 Drawing Sheets

METHOD AND SYSTEM FOR SCATTER CORRECTION IN X-RAY IMAGING

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of X-rays through the target volume, to acquire image data and to construct tomographic images (e.g., three-dimensional representations of the interior of the human body or of other imaged structures). However, various physical limitations or constraints on acquisition may result in artifacts or other imperfections in the reconstructed image.

For example, in a wide-cone X-ray CT system, the ratio of the signal attributable to scatter relative to the primary signal may be high. Such scatter may manifest as either noise or artifacts in the reconstructed images. Proper scatter mitigation may include both scatter rejection and the use of anti-scatter grids. One-dimensional (1D) grids may be employed to help reduce scatter, with the height of the 1D grid determining the degree of scatter reduction. To reject more scatter, two-dimensional (2D) grids can be used, but at a price of complexity and cost. However, even using anti-scatter grids, the presence of scatter may result in image artifacts in the reconstructed images.

BRIEF DESCRIPTION

In one embodiment, a method for estimating scatter is provided. In accordance with this method, an initial volume is generated based on X-ray transmission from a source to a detector. A plurality of voxels is characterized within the initial volume based on material type. A density integrated volume is generated based on the plurality of voxels characterized based on material type. One or more scattered X-rays are tracked beginning at the detector and proceeding toward the source to generate a scatter profile for a plurality of discrete locations on the detector.

In a further embodiment, an image processing system is provided. The image processing system includes a memory storing one or more routines and a processing component configured to execute the one or more routines stored in the memory. The one or more routines, when executed by the processing component: characterize a plurality of voxels within an initial reconstructed volume based on material type; generate a density integrated volume based on the plurality of voxels characterized based on material type; inversely track one or more scattered X-rays from a respective reception point to a respective transmission point to generate a scatter profile for a plurality of discrete locations on the detector; and generate one or more scatter corrected images using the scatter profile or a kernel derived based at least in part upon the scatter profile.

In an additional embodiment, one or more non-transitory computer-readable media are provided. The one or more non-transitory computer-readable media encode one or more routines which, when executed by a processor, cause the processor to perform acts comprising: generating a density integrated volume, wherein each voxel of the density integrated volume represents the density integration from a source of X-rays to the respective voxel; generating a scatter profile by tracking one or more scattered X-rays from respective locations on a detector to the source through the density integrated volume; and correcting for scatter in one or more reconstructed images using the scatter profile or a kernel derived based at least in part upon the scatter profile.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

In instances where one-dimensional or two-dimensional anti-scatter grids are employed, computational scatter correction based on image processing may still be utilized to further suppress image artifacts due to scatter and to achieve good image quality. Without an accurate scatter correction algorithm, the resulting image artifacts attributable to scatter effects can be detrimental. In the present disclosure, a physics model based correction algorithm and its use for scatter artifact suppression is described.

Figure 1:
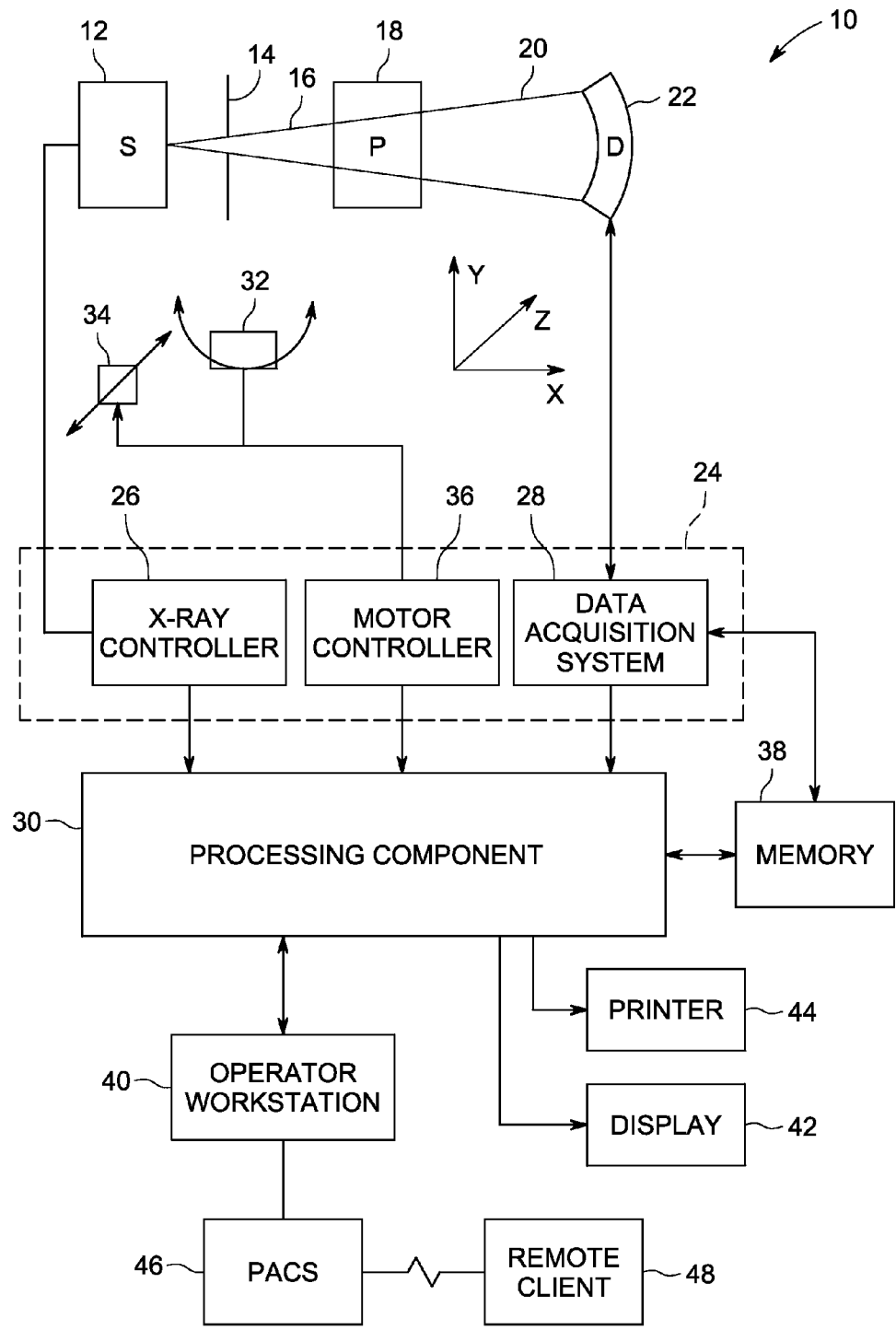
FIG. 1 is a diagrammatical view of a CT imaging system for use in producing images in accordance with aspects of the present disclosure.

With this in mind, an example of a computed tomography (CT) imaging system 10 designed to acquire X-ray attenuation data at a variety of views around a patient and suitable for tomographic reconstruction is provided in FIG. 1. In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical or other images.

The collimator 14 permits X-rays 16 to pass into a region in which a patient 18, is positioned. In the depicted example, the X-rays 16 are collimated to be a cone-shaped beam, i.e., a cone-beam, that passes through the imaged volume. A portion of the X-ray radiation 20 passes through or around the patient 18 (or other subject of interest) and impacts a detector array, represented generally at reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x, y-plane about the patient. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that X-ray attenuation data may be obtained at a variety of views relative to the subject. In the present context, system controller 24 may also includes signal processing circuitry, associated memory circuitry for storing programs and routines executed by the computer (such as routines for executing image processing and/or scatter correction techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction and/or scatter correction, as described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

With the foregoing discussion of a representative CT imaging system in mind, it will be appreciated that, depending on the scatter suppression needs of a given system, the correction algorithms employed can vary. In certain implementations, the scatter correction may be directly applied to each of the projections or using a second pass algorithm where the scatter profiles are computed by tracking rays through the volume. In accordance with the present discussion, scatter correction is performed based on the initial image volume with scatter ray tracking, but with the elimination of one integration loop during the scatter ray tracking process. Elimination of the integration loop may result in improvements in computational time, such as reducing computational time expended on scatter correction by a factor of one hundred or more.

Unlike projection based scatter correction approaches, where an approximate scatter profile is computed based on the measured projection, accurate scatter profile capture in accordance with present embodiments utilizes the entire image volume. In these embodiments, at each view angle, the X-ray from the source is tracked when it interacts with the material in the volume. The interaction creates scattered X-rays, in all the possible directions. These rays are again either attenuated or scattered, creating cascaded scatter events. In X-ray CT, the single event where only one scatter interaction is encountered, accounts for the most severe image artifact, since this type of events contains some level of high frequency content in the scatter profile.

In a conventional tracing approach for a single event, ray casting from the source may be performed. The primary ray attenuation may be traced as the ray penetrates the volume. Interaction at a given point in the volume may be computed using proper differential cross-sections. The scattered ray at a given angle is traced and its attenuation computed until it exits the volume. The intensity of the scattered ray is then accumulated. These steps may be used to compute the scatter event for one primary ray at a given interaction point in the volume and scattered to a given angle. These steps may be repeated for all incident rays, all interaction points, and all the directions to which the scattered ray is scattered.

Figure 2:
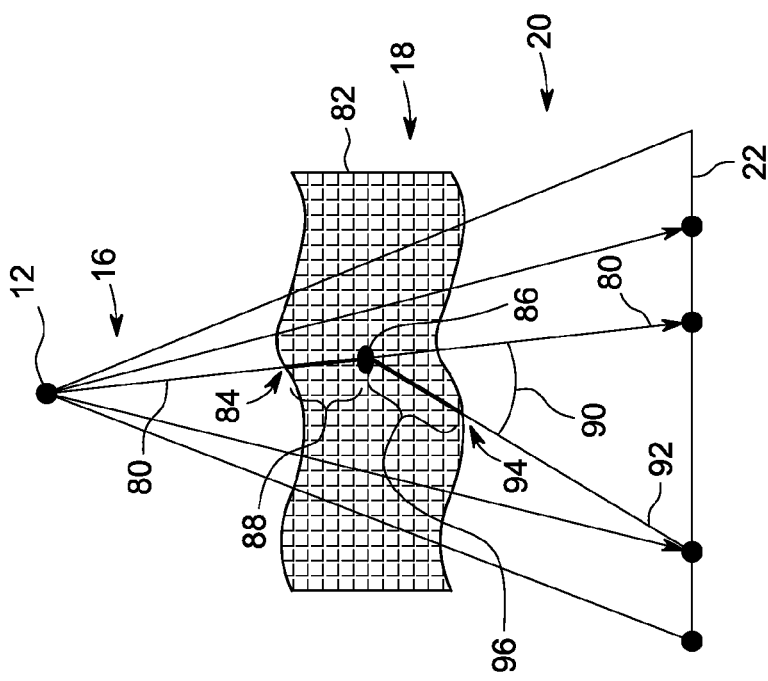
FIG. 2 depicts top-down ray tracking for scattered rays.

These conventional steps are depicted in FIG. 2, where a first primary ray 80 interacts with a volume 82 (e.g., patient 18) at a first surface point 84. At a first point of interaction 86, the first primary ray 80 has been attenuated by the material composing the volume 82 along line segment 88, defined by the first surface point 84 and the first point of interaction 86. The attenuation tracking along line segment 88 is an integration process. At first interaction point 86, the intensity of the first primary beam 80, the energy spectrum, the material type and density at first interaction point 86, and the scatter angle 90 determine the scattered ray 92 intensity along the line segment 96 from first interaction point 86 to volume exit point 94. The final scattered beam intensity by first interaction point 86 is again subjected to the attenuation along line segment 96, which is another integration process.

Figure 3:
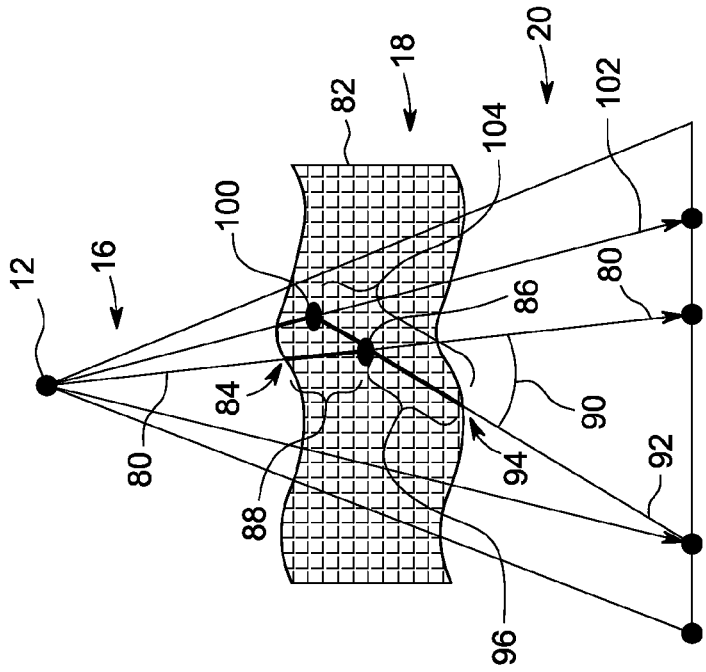
FIG. 3 depicts further aspects of top-down ray tracking for scattered rays.

Turning to FIG. 3, in accordance with conventional processing, if we take a second point of interaction 100 associated with second primary ray 102, the same integration process is repeated for attenuation integration along line segment 104. As will be appreciated, part of the integration along line segment 104, the attenuation along line segment 96, is already computed with respect to the first primary ray 80 scatter event. The redundancy of integration in this conventional approach is intrinsic to the top-down (from source 12 to scattering or interaction point) ray tracking process, which increases the computational time for scatter capture. Although, the redundant integration value along line segment 96 can be buffered in computer memory for later use, the top-down tracking strategy employs computational resources to match the second interaction point 100 to the extended line segment 96 in order to use the buffered line segment 96 integration data, creating complex memory buffer and line matching.

Figure 4:
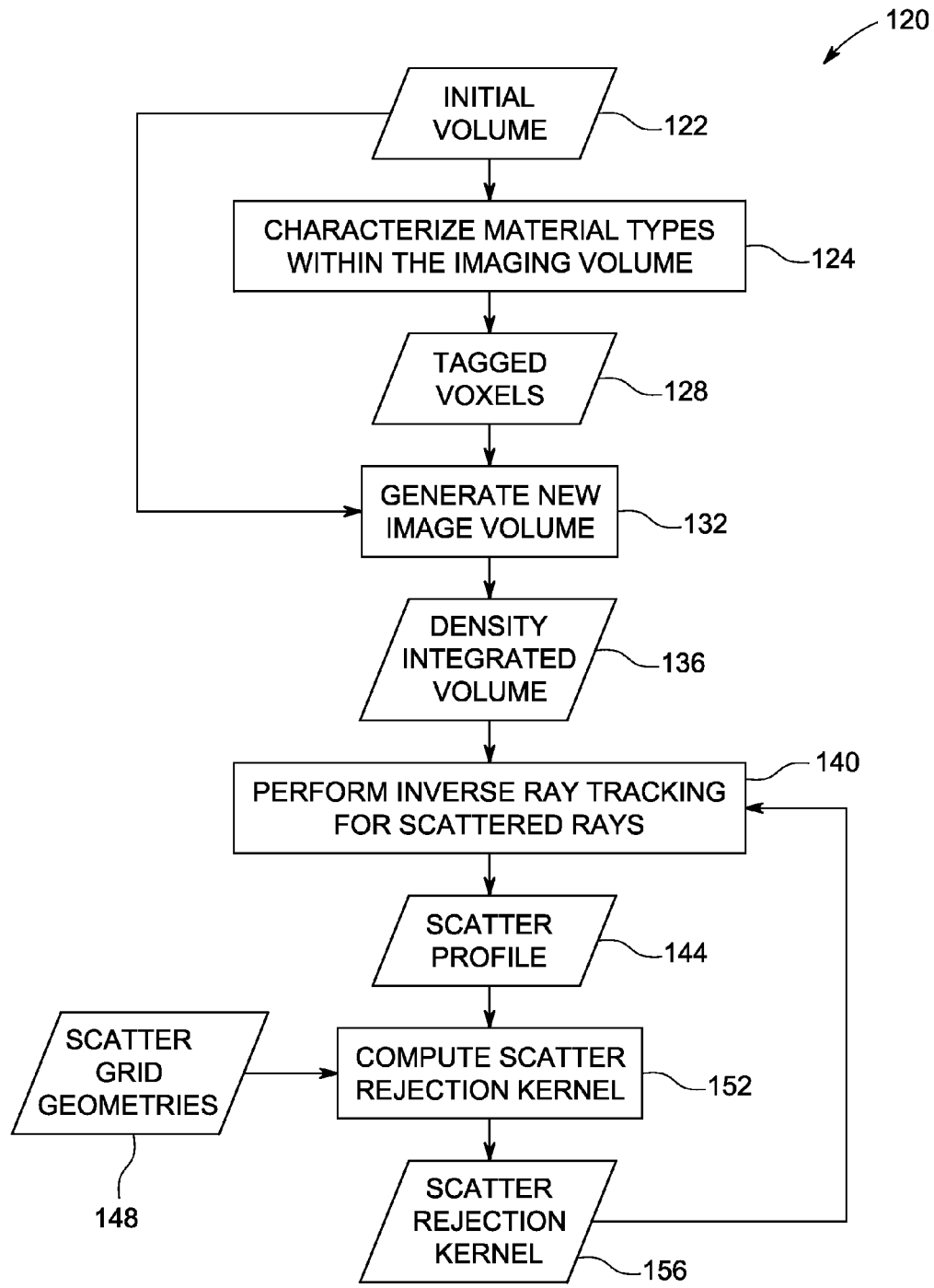
FIG. 4 depicts a flow chart depicting steps of one implementation for inverse ray tracking for scattered rays in accordance with aspects of the present disclosure.

The present approach employs inverse ray tracking to avoid the integration redundancy note above. In such an inverse ray tracking approach, ray tracking begins at the detector 22. In accordance with one implementation of an inverse ray tracking algorithm, the following steps, as depicted in flowchart 120 of FIG. 4, may be employed. Turning to FIG. 4, an initial volume 122 is reconstructed, such as based on a scan of a patient or object of interest. In the depicted implementation, the different material types within the initial volume 122 are characterized (block 124).

For example, in a medical imaging context, there are a few distinct types of materials that are or may be present inside a human body (e.g., soft tissue, bone, air, contrast agent, metal implants, and so forth). These materials often appear with relatively large volume, thus dominating the overall scatter profile, while small amounts of other materials, such as calcium do not have much impact to the final scatter profile. Therefore, in a medical imaging context, the voxels of the initial volume corresponding to a given material may be tagged (i.e., tagged voxels 128) or otherwise associated with information characterizing a given voxel based on material type or composition.

The material characterization 124 can be based on the output of segmentation algorithms and/or based on observed intensity values or differences (e.g., observed Hounsfeld unit (HU) value differences) as compared to threshold values associating observed intensities or intensity differences with particular materials. After the characterization, the voxel is tagged, as discussed above, with proper differential cross-sections for the identified material type, including contribution from both Compton and coherent scattering.

Figure 6:
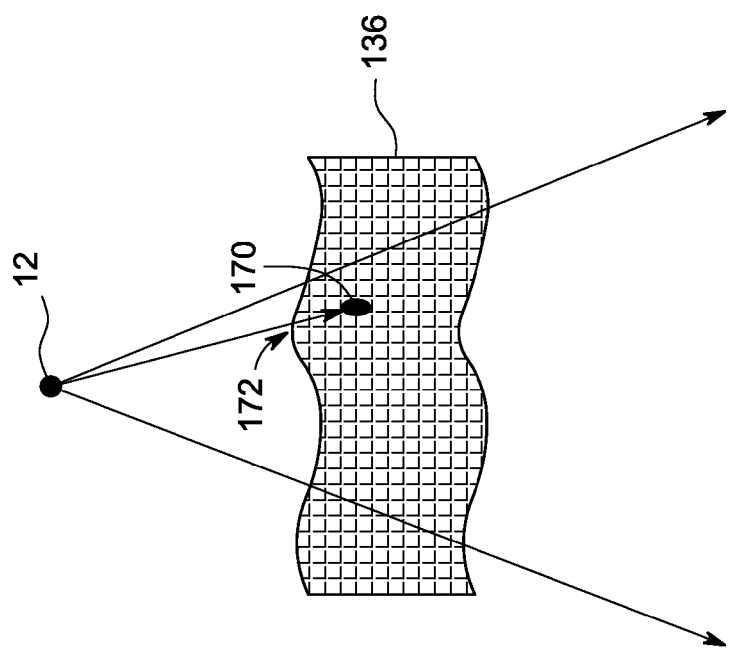
FIG. 6 depicts a density integrated volume in accordance with aspects of the present disclosure.
Figure 5:
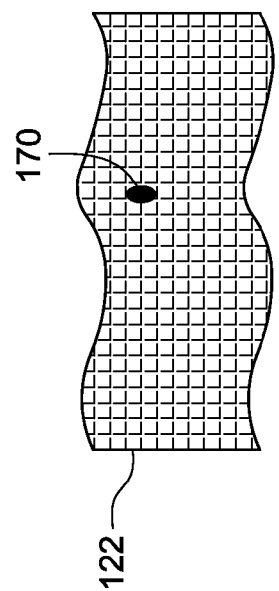
FIG. 5 depicts an initial reconstructed volume in accordance with aspects of the present disclosure.

Based on the initial image volume 122, a new image volume (i.e., density integrated volume 136) is generated (block 132). The density integrated volume 136 is the density integration along the primary ray direction. In the density integrated volume 136, each voxel represents the density integration from the source 12 down to each respective voxel, creating a primary beam attenuation map for subsequent use. By way of example, and turning to FIGS. 5 and 6, FIG. 5 depicts initial volume 122 where $u_{cal}$ is the apparent attenuation coefficient at location (x, y, z) 170 after spectral calibration and d(x, y, z) is the density as location (x, y, z) 170. In practice, the product of $u_{cal}$ and d is generated by the image reconstruction process, with the projection data corrected by spectral calibration and HU values normalized to water. That is, the image reconstruction process used to generate the initial volume 122 typically assigns a value at each voxel, such as at the voxel as at the voxel associated with location 170, that is the product of the attenuation coefficient $u_{cal}$ and the density d at the respective voxel location.

However, turning to FIG. 6, the voxel values in the density integrated volume 136 are instead based on the density integration value corresponding to the distance a ray travels through the material, such as between the voxel location 170 and the material surface entry point 172 (e.g., $\Sigma u_{cal} d(x,y,z)$ from location 172 to location 170 in the depicted example).

Further, based on the density integration value from location 170 to upstream, the beam energy spectrum $S_A(E)$ at location 170 is also determined by incorporating the incident beam spectrum $S_0(E)$ and the density integration value from location 170 to location 172, expressed as:

$$S_A(E) = S_0(E)\exp(-u(E)*d(x,y,z)) \quad (1)$$

where u(E) is the mass attenuation coefficient of a given material.

Figure 7:
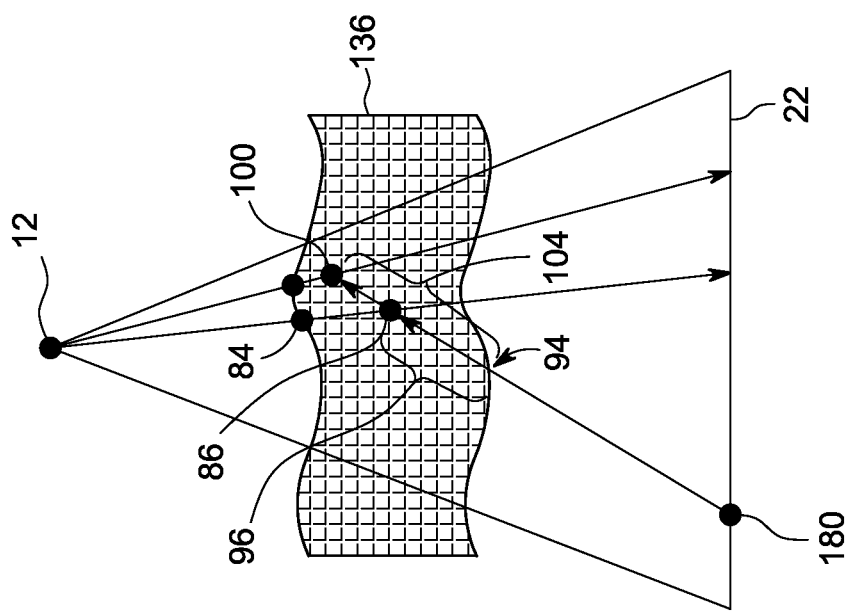
FIG. 7 depicts inverse ray tracking of a scattered ray in accordance with aspects of the present disclosure.

Contrary to conventional approaches (i.e., top-down tracking for scatter events), certain present embodiments employ a bottom-to-top tracking scheme to provide inverse ray integration tracking for scattered rays (i.e., block 140), thereby generating a scatter profile 144. An example of such an approach is depicted in FIG. 7, which depicts inverse ray tracking for a single ray.

Starting from a receiving point 180 for scatter detection, the density integration from volume exit point 94 to first interaction point 86 (i.e., for line segment 96) is computed, and scatter intensity V(A) at first interaction point 86 can be expressed as:

$$V(A) = \exp\left(-\sum_{over\_CA} d(x, y, z)u_{eff}\right) * \text{density}(A) * K(\theta 1, S(E)) * \quad (2)$$

$$\exp\left(-\sum_{over\_BA} d(x, y, z)u_{eff}\right)$$

$$= \exp\left\{-\sum_{over\_CA\_BA} d(x, y, z)u_{eff}\right\} *$$

$$\text{density}(A) * K(\theta 1, S(E))$$

where first volume exit point 94 is denoted as point C, first interaction point 86 is denoted as point A, and first surface point 84 is denoted as point B, density(A) is the density at point A (i.e., first interaction point 86), and K($\theta$1,S(E)) is the scatter differential cross section, determined by angle $\theta$1, and the effective beam energy S(E). In the energy range for medical X-ray CT, the differential cross-section is sensitive to S(E) due to the strong energy-dependence of coherent scatter. The effective attenuation coefficient u(E) is determined by:

$$u_{eff} = f(S_0(E)), \Sigma_{over\_CA\_BA} d(x,y,z) u_{cal} \quad (3)$$

where function f( ) is derived based on known X-ray attenuation physics.

After obtaining scatter intensity by first interaction point 86 to the given receiving point 180, the tracking continues to second interaction point 100. In this step, only integration from first interaction point 86 to second interaction point 100 is needed, and it is accumulated to the existing integration from first volume exit point 94 to first interaction point 86 to obtain the attenuation of scattered signal along line segment 104, eliminating the redundancy of computing the integration between the first volume exit point 94 to first interaction point 86 a second time. Such process is continued until the projected ray extends outside the image volume, i.e., density integrated volume 136.

Figure 8:
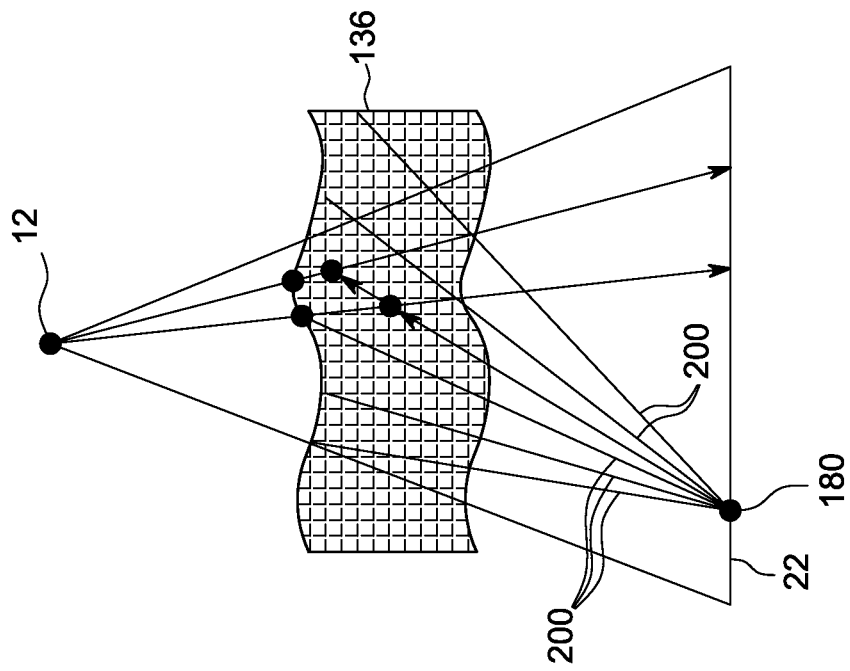
FIG. 8 depicts inverse ray tracking of additional scattered rays in accordance with aspects of the present disclosure.

Upon completing of tracking scatter intensity along one ray, other rays can be tracked the same way, as shown in FIG. 8. In the depicted example, the new tracking lines 200 are originated form the same receiving point 180, and uniformly distributed across the density integrated volume 136 to complete scatter intensity at the given receiving point 180. By repeating this process for various receiving points, a scatter profile 144 may be generated for the respective detector locations. In one implementation, due to the limited bandwidth of scatter profile 144, discrete receiving points can be arranged uniformly at various positions at the receiving side, and later interpolated to line up with the detector pixels for scatter correction.

Turning back to FIG. 4, in the depicted example an additional step of computing (block 152) a scatter rejection kernel 156 is depicted. In particular, in a system with anti-scatter grids, arranged in either 1D or 2D directions, the scatter rejection kernel 156 may be computed (block 152) as a function of the incident scattered X-rays (as determined from the scatter profile 144) to the anti-scatter grid's geometry 148. This scatter rejection kernel 156 may be applied to the computation of the scatter profile 144 to update or generate a scatter profile received by the detection system, which is subtracted from the measured projections for scatter correction.

Technical effects of the invention include generation of a density integrated volume based on an initial volume and material type characterization of the initial volume. Further technical effects include the generation of a scatter profile for an X-ray system, such as a CT system, by tracing scattered X-rays from locations on the detector to the X-ray source, i.e., inverse tracking. Further technical effects include the generation of a scatter rejection kernel based on a scatter profile and a scatter grid geometry.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for estimating scatter, comprising:
   generating an initial volume based on X-ray transmission from a source to a detector;
   characterizing a plurality of voxels within the initial volume based on material type;
   generating a density integrated volume based on the plurality of voxels; and
   tracking one or more scattered X-rays beginning at the detector and proceeding toward the source to generate a scatter profile for a plurality of discrete locations on the detector.

2. The method of claim 1, comprising:
   correcting scatter in one or more reconstructed images using the scatter profile or a kernel based at least in part on the scatter profile.

3. The method of claim 1, wherein the plurality of voxels are characterized based on material types comprising soft tissue, bone, air, and contrast agent.

4. The method of claim 1, wherein characterizing the plurality of voxels comprises applying a segmentation algorithm, wherein the output of the segmentation algorithm corresponds to the different respective material types.

5. The method of claim 1, wherein characterizing the plurality of voxels comprises comparing observed intensity values or differences to respective thresholds corresponding to the different respective material types.

6. The method of claim 1, wherein each voxel of the density integrated volume represents density integration from the source to the respective voxel.

7. The method of claim 1, comprising:
   generating a scatter rejection kernel based on at least the scatter profile and a scatter grid geometry associated with the detector.

8. The method of claim 7, comprising:
   updating the scatter profile based on the scatter rejection kernel to generate a revised scatter profile.

9. An image processing system, comprising:
   a memory storing one or more routines; and
   a processing component configured to execute the one or more routines stored in the memory, wherein the one or more routines, when executed by the processing component:
   characterize a plurality of voxels within an initial reconstructed volume based on material type;
   generate a density integrated volume based on the plurality of voxels;
   inversely track one or more scattered X-rays from a respective reception point to a respective transmission point to generate a scatter profile for a plurality of discrete locations on the detector; and generate one or more scatter corrected images using the scatter profile or a kernel based at least in part upon the scatter profile.

10. The image processing system of claim 9, wherein the one or more routines, when executed by the processing component:
generate the initial reconstructed volume based on X-ray transmission from a source comprising the respective transmission point to a detector comprising the respective reception point.

11. The image processing system of claim 9, wherein the plurality of voxels are characterized based on material types corresponding to a plurality of materials observed in medical images.

12. The image processing system of claim 9, wherein characterizing the plurality of voxels comprises applying a segmentation algorithm, wherein the output of the segmentation algorithm corresponds to the different respective material types.

13. The image processing system of claim 9, wherein characterizing the plurality of voxels comprises comparing observed intensity values or differences to respective thresholds corresponding to the different respective material types.

14. The image processing system of claim 9, wherein each voxel of the density integrated volume represents the density integration from the respective transmission point to the respective voxel.

15. The image processing system of claim 9, wherein the one or more routines, when executed by the processing component:
generate a scatter rejection kernel based on at least the scatter profile and a scatter grid geometry.

16. One or more non-transitory computer-readable media, encoding one or more routines which, when executed by a processor, cause the processor to perform acts comprising:
generating a density integrated volume, wherein each voxel of the density integrated volume represents the density integration from a source of X-rays to the respective voxel;
generating a scatter profile by tracking one or more scattered X-rays from respective locations on a detector to the source through the density integrated volume; and
correcting for scatter in one or more reconstructed images using the scatter profile or a kernel based at least in part upon the scatter profile.

17. The one or more non-transitory computer-readable media of claim 16, wherein the density integrated volume is generated using an initial volume that has been characterized based on material type.

18. The one or more non-transitory computer-readable media of claim 17, wherein the initial volume is characterized based on material type using a segmentation process or thresholding based on intensity values or intensity differences.

19. The one or more non-transitory computer-readable media of claim 16, further encoding a routine which, when executed by a processor, causes the processor to perform the act of:
generating a scatter rejection kernel based on at least the scatter profile and a scatter grid geometry associated with the detector.

20. The one or more non-transitory computer-readable media of claim 16, further encoding a routine which, when executed by a processor, causes the processor to perform the act of:
generating an initial volume based on X-ray transmission from the source to the detector.

* * * * *